(12) United States Patent
Jang et al.

(10) Patent No.: US 8,785,924 B2
(45) Date of Patent: Jul. 22, 2014

(54) HIGH-SENSITIVITY TRANSPARENT GAS SENSOR AND METHOD FOR MANUFACTURING THE SAME

(75) Inventors: Ho Won Jang, Daegu (KR); Seok Jin Yoon, Seoul (KR); Jin Sang Kim, Seoul (KR); Chong Yun Kang, Seoul (KR); Ji Won Choi, Seoul (KR); Hi Gyu Moon, Gyeonggi-do (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 13/542,874

(22) Filed: Jul. 6, 2012

(65) Prior Publication Data

US 2013/0146865 A1 Jun. 13, 2013

(30) Foreign Application Priority Data

Dec. 12, 2011 (KR) ........................ 10-2011-0132714

(51) Int. Cl.
*H01L 29/82* (2006.01)

(52) U.S. Cl.
USPC ...... 257/43; 257/253; 257/435; 257/E29.068; 257/E21.002; 977/953

(58) Field of Classification Search
USPC ............ 257/43, 253, 435, E29.068, E21.002; 977/953
See application file for complete search history.

(56) References Cited

U.S. PATENT DOCUMENTS

| 4,781,798 | A | 11/1988 | Gough | |
|---|---|---|---|---|
| 7,976,950 | B2 * | 7/2011 | Okai et al. | 428/408 |
| 7,989,851 | B2 * | 8/2011 | Lu et al. | 257/252 |
| 2007/0210349 | A1 * | 9/2007 | Lu et al. | 257/252 |
| 2011/0008245 | A1 * | 1/2011 | Park et al. | 423/561.1 |
| 2012/0051976 | A1 * | 3/2012 | Lu et al. | 422/69 |
| 2012/0266658 | A1 * | 10/2012 | Akiyama et al. | 73/31.05 |
| 2013/0061660 | A1 * | 3/2013 | Kasama et al. | 73/31.06 |
| 2013/0075690 | A1 * | 3/2013 | Briman et al. | 257/9 |
| 2013/0078476 | A1 * | 3/2013 | Riman et al. | 428/469 |
| 2013/0146865 | A1 * | 6/2013 | Jang et al. | 257/43 |
| 2013/0209781 | A1 * | 8/2013 | Bellman et al. | 428/312.6 |

FOREIGN PATENT DOCUMENTS

| JP | 05-179439 | A | 7/1993 |
|---|---|---|---|
| JP | 10-010048 | A | 1/1998 |
| JP | 2002-170557 | A | 6/2002 |
| KR | 100316389 | B1 | 11/2001 |
| KR | 100812357 | B1 | 3/2008 |
| KR | 1020090046179 | A | 5/2009 |
| KR | 100932596 | B1 | 12/2009 |
| KR | 1020100067972 | A | 6/2010 |
| KR | 100989611 | B1 | 10/2010 |
| KR | 1020110056694 | A | 5/2011 |

\* cited by examiner

*Primary Examiner* — Michael Shingleton
(74) *Attorney, Agent, or Firm* — Ladas & Parry LLP (57) ABSTRACT

Disclosed are a high-sensitivity transparent gas sensor and a method for manufacturing the same. The transparent gas sensor includes a transparent substrate, a transparent electrode formed on the transparent substrate and a transparent gas-sensing layer formed on the transparent electrode. The transparent gas-sensing layer has a nanocolumnar structure having nanocolumns formed on the transparent electrode and gas diffusion pores formed between the nanocolumns.

9 Claims, 14 Drawing Sheets

HIGH-SENSITIVITY TRANSPARENT GAS SENSOR AND METHOD FOR MANUFACTURING THE SAME

CROSS-REFERENCE TO RELATED APPLICATIONS

This application claims priority under 35 U.S.C. §119 to Korean Patent Application No. 10-2011-0132714, filed on Dec. 12, 2011, in the Korean Intellectual Property Office, the disclosure of which is incorporated herein by reference in its entirety.

BACKGROUND

1. Field

The present disclosure relates to a high-sensitivity transparent gas sensor and a method for manufacturing the same. More particularly, the present disclosure relates to a high-sensitivity transparent gas sensor having high light transmittance as well as superior gas sensitivity even when no heat is applied from outside and consuming less power, and a method for manufacturing the same.

2. Description of the Related Art

Gas sensors for detecting toxic gas, explosive gas, environmentally harmful gas, etc. are important in many fields including health care, national defense, counter-terrorism and environment. Researches are consistently ongoing on the gas sensors. In particular, researches are being carried out on the semiconductor gas sensor wherein gas-sensitive metal oxide film is used.

In general, a semiconductor gas sensor comprises a substrate, an electrode formed on the substrate, and a gas-sensing layer formed on the electrode. The substrate is made of silicon or alumina, and the electrode is made of noble metal such as platinum (Pt), gold (Au), etc. And, the gas-sensing layer is made of metal oxide film. The semiconductor gas sensor detects the presence, concentration, etc. of a gas based on the change in electrical resistance of the metal oxide film (gas-sensitive material) resulting from adsorption and oxidation/reduction reaction of the gas on the surface of the metal oxide film. Usually, the gas-sensitive material is a metal oxide semiconductor material such as zinc oxide (ZnO), tin oxide ($SnO_2$), tungsten oxide ($WO_3$) titanium oxide ($TiO_2$), indium oxide ($In_2O_3$), etc.

Recently, efforts are being made to improve gas sensitivity by increasing the specific surface area of the gas-sensing layer. For instance, semiconductor gas sensors have been suggested.

Since the semiconductor gas sensor operates on a simple principle, is compact in volume and costs little, it is expected to capable of replacing the existing electrochemical or optical gas sensors.

Furthermore, if a semiconductor gas sensor having high sensitivity for the gas to be detected and consuming less power could be manufactured, it may be mounted on a mobile phone or other mobile devices, thereby further enhancing the functionality of the mobile devices. In addition, if a transparent semiconductor gas sensor could be manufactured, it may be mounted on transparent displays and transparent mobile phones which will be realized in near future as well as on car windowpanes.

However, no transparent gas sensor with excellent light transmittance in the visible region without sacrificing performance has been reported as yet. In addition, despite the many advantages over the electrochemical or optical gas sensors, the existing semiconductor gas sensors are not widely used for practical applications for the following reasons.

First, the semiconductor gas sensor is opaque and expensive. Specifically, since the substrate is made of silicon or alumina and the electrode is made of an opaque noble metal such as platinum (Pt), gold (Au), etc., the gas sensor is not transparent. And, the noble metal such as platinum (Pt) or gold (Au) used in the electrode is expensive. In addition, since the process of forming the electrode (metal layer) and the process of depositing the gas-sensing layer (metal oxide film) is not compatible with each other, large-scale production is difficult.

Further, the gas sensor requires a heat source for operation. That is to say, the existing semiconductor gas sensor has good gas sensitivity only when heat of 200-400° C. is supplied from an external heat source such as a metal heater. Besides, the existing semiconductor gas sensor lacks reliability due to inaccurate change in resistance of the gas-sensitive material because of high contact resistance between the metal (e.g., Pt) of the electrode and the gas-sensing layer (metal oxide film). In addition, it consumes a lot of power. For example, power consumption of a general existing thick-film gas sensor is about 1 mW, and that of a thin-film gas sensor based on microelectromechanical systems (MEMS) is about 10-200 mW. Above all things, since the existing semiconductor gas sensor is opaque, as described above, it is inapplicable to transparent electronic devices such as transparent displays, transparent mobile phones, etc. or transparent products such as windowpanes of cars.

SUMMARY

To realize a transparent semiconductor gas sensor, the following technical problems have to be solved.

First, a substrate used as a support of the gas sensor should be transparent, unlike the existing silicon or alumina substrate. Second, an electrode should also be transparent, unlike opaque metal. Third, light scattering should be avoided while ensuring transparency and, above all, gas sensitivity should be comparable or better as compared to the existing opaque gas sensor.

In addition, the transparent semiconductor gas sensor should have good gas sensitivity even without an external heat source such as a metal heater. Further, it needs to be inexpensive and consume less power.

The present disclosure is directed to providing a high-sensitivity transparent gas sensor being transparent with high light transmittance, having superior gas sensitivity even when no heat is applied from outside by forming a gas-sensing layer to have a nanocolumnar structure and consuming less power, and a method for manufacturing the same.

In one general aspect, the present disclosure provides a transparent gas sensor, including: a transparent substrate; a transparent electrode formed on the transparent substrate; and a transparent gas-sensing layer formed on the transparent electrode, wherein the transparent gas-sensing layer has a nanocolumnar structure having nanocolumns formed on the transparent electrode and gas diffusion pores formed between the nanocolumns.

The nanocolumns may be arranged on an x-y plane on the transparent electrode such that the gas diffusion pores are formed between the nanocolumns arranged in one of the x and y directions and the nanocolumns arranged in the other direction are connected with each other. In addition, the nanocolumns may be formed to be inclined, for example, with an angle of 60-89°.

In another general aspect, the present disclosure provides a method for manufacturing a transparent gas sensor, including: a first step of forming a transparent electrode on a transparent substrate; and a second step of forming a transparent gas-sensing layer on the transparent electrode, wherein, in the second step, the transparent gas-sensing layer is formed to have a nanocolumnar structure having nanocolumns formed on the transparent electrode and gas diffusion pores formed between the nanocolumns.

Since the transparent gas sensor according to the present disclosure is transparent, it can be mounted on transparent electronic devices or transparent products such as windowpanes. Further, it exhibits superior gas sensitivity even without heat supply from outside owing to the excellent response provided by the nanocolumnar structure. In addition, it can be provided at low cost and can be mounted on mobile devices such as mobile phones because of low power consumption.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION OF EMBODIMENTS

Hereinafter, exemplary embodiments will be described in detail with reference to the accompanying drawings.

Figure 1:
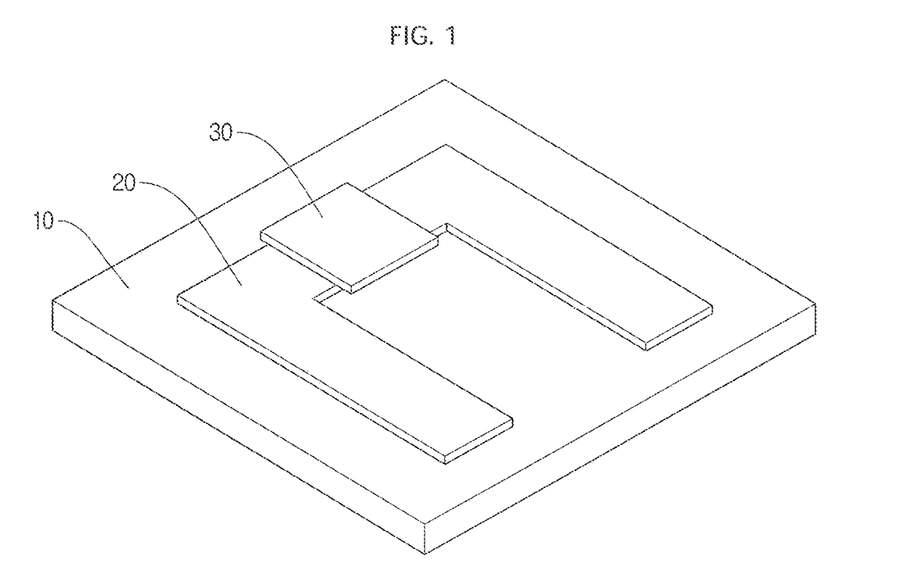
FIG. 1 is a perspective view of a transparent gas sensor according to an exemplary embodiment of the present disclosure.

First, referring to FIG. 1, a transparent gas sensor according to an exemplary embodiment of the present disclosure comprises a substrate 10, an electrode 20 formed on the substrate 10, and a gas-sensing layer 30 formed on the electrode 20. The substrate 10, the electrode 20 and the gas-sensing layer 30 are transparent. For example, they may exhibit light transmittance of at least 80%, specifically at least 90%, in the visible region.

The substrate 10 may be any one that is capable of supporting the electrode 20 and the gas-sensing layer 30 and is transparent, without particular limitation. For example, the substrate 10 may be a transparent substrate selected from glass, sapphire, quartz, metal oxide (e.g., MgO) and plastic substrates. Specifically, the substrate 10 may be selected from a glass substrate, a sapphire substrate, a quartz substrate, an MgO substrate or a transparent plastic film, which are advantageous in terms of transparency and cost. The substrate 10 may have a thickness of, for example, 0.05-10 mm, although not limited thereto.

The electrode 20 may be any one which is transparent and conductive. For example, the electrode 20 may be selected from conductive metal oxide film or carbon film.

The electrode 20 may be a metal oxide film which is a conductive oxide film comprising at least one metal selected from indium (In), tin (Sn), zinc (Zn), aluminum (Al), niobium (Nb), titanium (Ti) and gallium (Ga). In specific embodiments, the electrode 20 may be an indium (indium oxide)-, tin (tin oxide)- or zinc (zinc oxide)-based conductive oxide film. More specifically, the electrode 20 may be an oxide film comprising, for example, indium tin oxide (ITO), fluorine tin oxide (FTO), aluminum zinc oxide (AZO), gallium zinc oxide (GZO), indium zinc oxide (IZO) or niobium titanium oxide (NTO). In addition, the electrode 20 may be a conductive carbon film comprising conductive carbon, e.g. graphene.

For example, the electrode 20 may have a thickness from 1 nm to 20 μm, more specifically from 10 nm to 1,000 nm.

Figure 2:
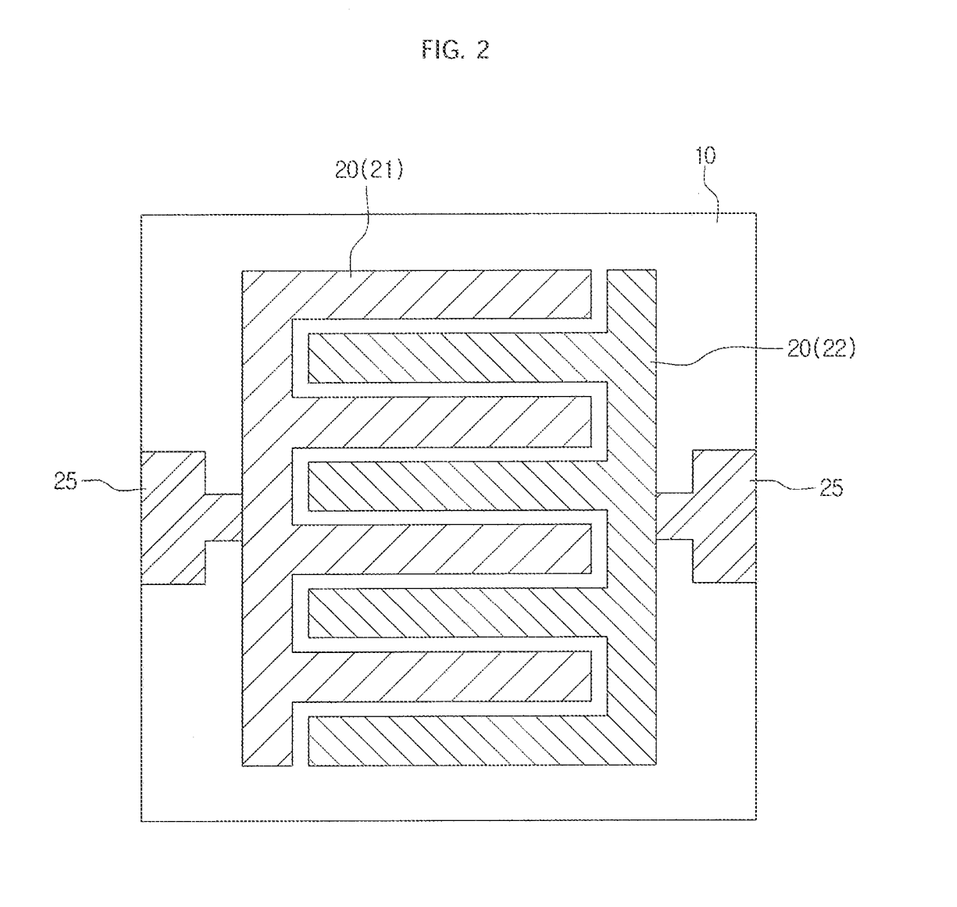
FIG. 2 is a plan view of an electrode pattern of a transparent gas sensor according to an exemplary embodiment of the present disclosure.

The electrode 20 may be formed on the substrate 10 by deposition, e.g. sputter deposition, electron beam deposition, chemical vapor deposition or wet deposition. And, the electrode 20 may have patterns of different shapes. FIG. 2 shows an exemplary pattern of the electrode 20. As shown in FIG. 2, the electrode 20 may have an interdigitated electrode (IDE) pattern. Specifically, the electrode 20 may have a finger (or comb)-shaped first pattern 21 and a second pattern 22 interdigitating therewith formed on the substrate 10, as shown in FIG. 2.

The gas-sensing layer 30 is not particularly limited as long as it is capable of detecting gas and is transparent. The gas-sensing layer 30 is formed at least on the electrode 20. Specifically, the gas-sensing layer 30 is formed at least on the electrode 20 so as to contact with the electrode 20. The gas-sensing layer 30 may be formed not only on the electrode 20 but also on the substrate 10. For example, if the electrode 20 has an IDE pattern as shown in FIG. 2, it may be formed not only on the patterned electrode 20 but also on the substrate 10 between the electrode 20 and the electrode 20.

The gas-sensing layer 30 detects gas. It is not particularly limited as long as it comprises a gas-sensitive material whose electrical resistance changes in response to adsorption and oxidation/reduction of gas molecules. The gas-sensing layer 30 may be one capable of detecting the presence and/or concentration of gas.

The gas-sensing layer 30 may comprise a commonly used metal oxide semiconductor material. Specifically, the gas-sensing layer 30 may comprise a metal oxide with energy band gap of at least 2.7 eV so as to provide high light transmittance in the visible region. More specifically, the gas-sensing layer 30 may comprise a metal oxide with band gap of 2.7-6.5 eV.

In an exemplary embodiment, the gas-sensing layer 30 may comprise at least one metal oxide selected from tungsten oxide ($WO_3$), tin oxide ($SnO_2$), niobium oxide ($Nb_2O_5$), zinc oxide (ZnO), indium oxide ($In_2O_3$), iron oxide ($Fe_2O_3$), titanium oxide ($TiO_2$), cobalt oxide ($Co_2O_3$) and gallium oxide ($Ga_2O_3$). These metal oxides are advantageous in terms of gas sensitivity and transparency owing to desirable band gap. The gas-sensing layer 30 may comprise one of the metal oxides described above, a mixture of two or more of them, or a material including at least one of them.

Figure 3:
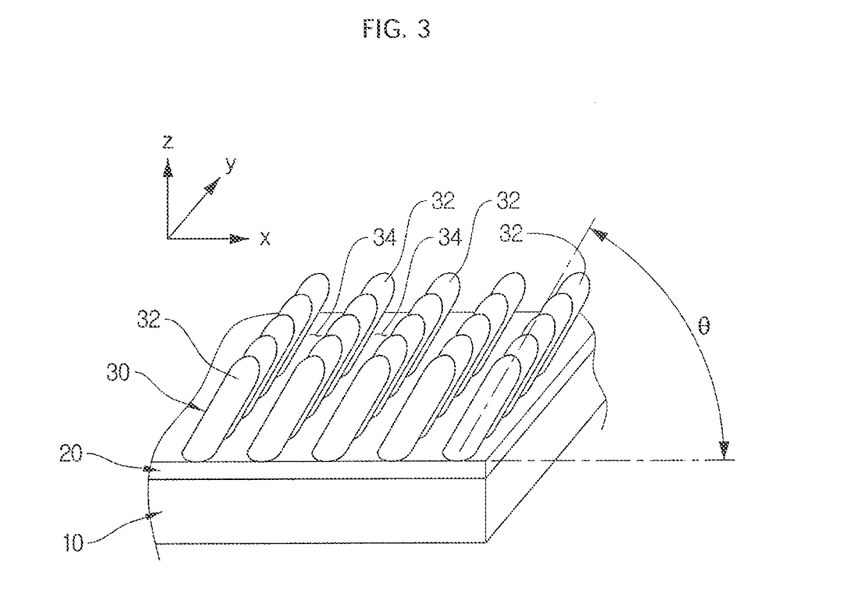
FIG. 3 is a perspective view for illustrating a gas-sensing layer of a transparent gas sensor according to an exemplary embodiment of the present disclosure.

The gas-sensing layer 30 has a nanocolumnar structure, which will be described referring to FIG. 3. FIG. 3 schematically illustrates an exemplary nanocolumnar structure.

Referring to FIG. 3, the gas-sensing layer 30 has a nanocolumnar structure comprising plurality of nanocolumns 32 formed on the electrode 20 and gas diffusion pores 34 formed between the nanocolumns 32. The nanocolumns 32 are arranged on an x-y plane on the electrode 20 to protrude in a z-axis direction.

The nanocolumns 32 may be arranged on the x-y plane such that the gas diffusion pores 34 are formed between the nanocolumns 32 arranged in one of the x and y directions and the nanocolumns 32 arranged in the other direction are connected with each other. In the embodiment shown in FIG. 3, the gas diffusion pores 34 are formed between the nanocolumns 32 arranged in the x direction, and the nanocolumns 32 arranged in the y direction are connected with each other.

For example, the nanocolumns 32 may have a thickness (diameter) not greater than 500 nm, more specifically 0.1-200 nm, although not being particularly limited thereto. And, the nanocolumns 32 may have a length (height in the z direction) not greater than 1,000 nm, more specifically 0.5-1,000 nm. And, the gas diffusion pores 34 formed between the nanocolumns 32 may have a size not greater than 500 nm, more specifically 0.1-300 nm. However, the size of the nanocolumns 32 and the pores 34 is not limited to the above description.

Referring to FIG. 3 again, the nanocolumns 32 may be formed to be inclined. That is to say, the nanocolumns 32 may be formed to have an angle θ smaller than 90° with the electrode 20. When the nanocolumns 32 are formed to have an angle θ smaller than 90° with the electrode 20, the volume of the pores 34 may be increased for a given thickness of the gas-sensing layer 30, i.e. for a given length (height) of the nanocolumns 32. As a result, gas may diffuse more easily and gas sensitivity may be increased. For example, the nanocolumns 32 may be formed to be inclined with an angle θ not greater than 89°, specifically 60-89°.

The nanocolumnar structure of the gas-sensing layer 30 provides superior gas sensitivity. Specifically, the plurality of nanocolumns 32 protruding on the electrode 20 provides increased specific surface area as well as superior gas sensitivity through improved gas diffusion owing to the pores 34. That is to say, superior gas sensitivity is achieved since the gas can diffuse not only to the surface of the nanocolumns 32 but also to the bottom portion of the nanocolumns 32 through the pores 34. In particular, superior gas sensitivity can be achieved thanks to excellent response even when no heat is supplied from outside, for example, by a metal heater.

The gas-sensing layer 30 is not particularly limited as long as it has the nanocolumnar structure. Specifically, the gas-sensing layer 30 may be a single layer having the nanocolumnar structure described above or a multilayer of two or more layers with the nanocolumnar structure formed on a common thin-film gas-sensing layer. For example, the gas-sensing layer 30 may have a thickness not greater than 5 µm, specifically 1-1,000 nm, although not being limited thereto.

The transparent gas sensor according to an exemplary embodiment of the present disclosure may further comprise common components in addition to the substrate 10, the electrode 20 and the gas-sensing layer 30 having the nanocolumnar structure described above. For example, it may further comprise an electrode pad 25 as shown in FIG. 2. The electrode pad 25 may be made of the same material as the electrode 20 and may be formed together during the deposition and patterning of the electrode 20.

The transparent gas sensor according to the present disclosure described above may be manufactured by various methods without particular limitation. For example, the transparent gas sensor may be manufactured by a method described below. Hereinafter, a method for manufacturing a transparent gas sensor according to an exemplary embodiment of the present disclosure will be described.

A method for manufacturing a transparent gas sensor according to an exemplary embodiment of the present disclosure comprises: a first step of forming an electrode 20 on a substrate 10; and a second step of forming a gas-sensing layer 30 on the electrode 20. The materials and types of the substrate 10, the electrode 20 and the gas-sensing layer 30 are the same as described above. And, all of them are transparent.

Specifically, the substrate 10 may be a transparent substrate selected from glass, sapphire, quartz, MgO and transparent plastic substrates. The electrode 20 may be formed using metal oxide or a carbon material such as graphene.

The first step may comprise: a deposition process of depositing metal oxide film on the substrate 10; and a patterning process of patterning the deposited metal oxide film. In the deposition process, the transparent conductive metal oxide film may be formed by, for example, sputter deposition, electron beam deposition, chemical vapor deposition or wet deposition. And, in the patterning process, the deposited metal oxide film may be patterned into an IDE pattern as shown in FIG. 2 via dry etching or wet etching.

In the second step, the gas-sensing layer 30 is formed to have a nanocolumnar structure having nanocolumns 32 formed on the electrode 20 and gas diffusion pores 34 formed between the nanocolumns 32.

Specifically, in the second step, the gas-sensing layer 30 may be formed by deposition like the electrode 20. In this case, the overall process may be more efficient. Specifically, the gas-sensing layer 30 may be formed by sputter deposition, electron beam deposition, chemical vapor deposition or wet deposition to have the nanocolumnar structure.

The gas-sensing layer 30 may be formed to have the nanocolumnar structure in various ways. For example, after disposing a mask having nanosized pores between the substrate 10 with the electrode 20 formed and a sputter gun, deposition may be performed to form the nanocolumnar structure having the nanocolumns 32 and the gas diffusion pores 34. Specifically, glancing angle deposition may be employed, the principle of which will be described referring to FIG. 4.

Figure 4:
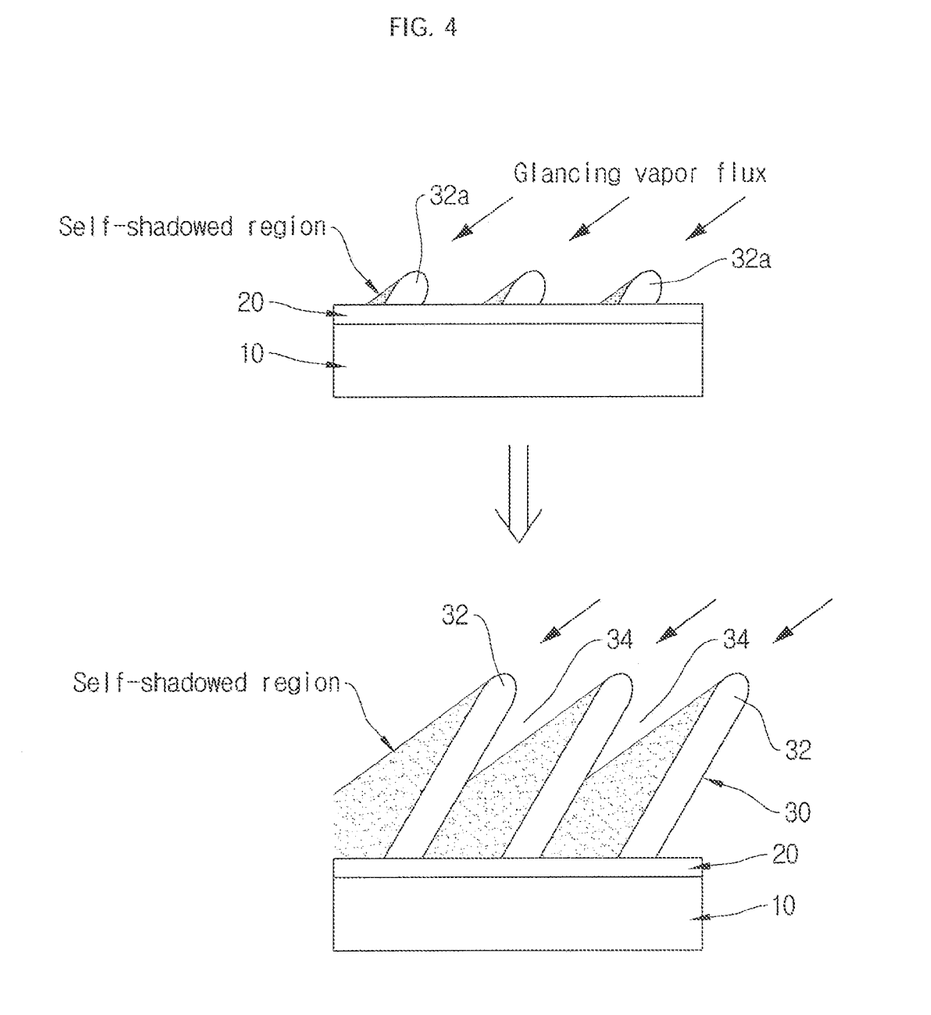
FIG. 4 is a cross-sectional view for illustrating a method for manufacturing a transparent gas sensor according to an exemplary embodiment of the present disclosure.

Referring to FIG. 4, metal oxide (gas-sensitive material) is deposited on the electrode 20 by sputtering such that the sputtered metal oxide flux is deposited on the electrode 20 with a predetermined angle to form metal oxide nuclei 32a. Subsequently, metal oxide is grown on the nuclei 32a by further glancing angle deposition to form the nanocolumns 32. The gas diffusion pores 34 are formed between the nanocolumns 32 as a result of the self-shadowing effect. That is to say, the gas diffusion pores 34 are formed in the self-shadowed region shown in FIG. 4 since deposition by the flux does not occur there.

When depositing the metal oxide flux with a predetermined angle, the angle between the substrate 10 and the sputter gun may be maintained at 90° or 180°, more specifically smaller than 90°. For example, the angle between the substrate 10 and the sputter gun may be maintained at 60-89°.

Since the gas sensor of the present disclosure has superior transparency, it can be easily mounted on transparent electronic devices or transparent products such as windowpanes. Furthermore, as described earlier, it has superior gas sensitivity even without heat supply from outside owing to excellent response provided by the nanocolumnar structure. And, the transparent gas sensor can be produced in large scale at low cost since the production processes of the electrode 20 and the gas-sensing layer 30 are compatible with each other. In addition, since it consumes less power, it can be mounted on mobile devices such as mobile phones.

The examples and comparative examples of the present disclosure will now be described. The following examples are for illustrative purposes only and not intended to limit the scope of this disclosure.

Example 1

First, a glass substrate was mounted on a sputtering apparatus. Then, indium tin oxide (ITO) film was deposited on the glass substrate by axis RF sputtering. The ITO film was deposited for about 30 minutes using a sputter gun with an ITO target comprising 90 wt % $In_2O_3$ and 10 wt % $SnO_2$ loaded, with 150 W RF power using pure argon (Ar) gas at 10 mTorr. Subsequently, the ITO film was dry etched to form a patterned transparent electrode in the form of an interdigitated electrode (hereinafter, referred to as 'IDE transparent electrode').

Then, tungsten oxide ($WO_3$) layer was deposited on the patterned IDE transparent electrode as a gas-sensing layer by axis RF sputtering as described above. When depositing the $WO_3$ layer, the sputtering was performed with the angle between a sputter gun with a $WO_3$ target loaded and a substrate holder maintained at about 85°. As a result, a transparent gas sensor having $WO_3$/ITO/glass layer wherein the $WO_3$ layer has a nanocolumnar structure was manufactured.

Comparative Example 1

A transparent gas sensor was manufactured as in Example 1, except for forming the $WO_3$ layer as a flat thin film without having the nanocolumnar structure.

Figure 5:
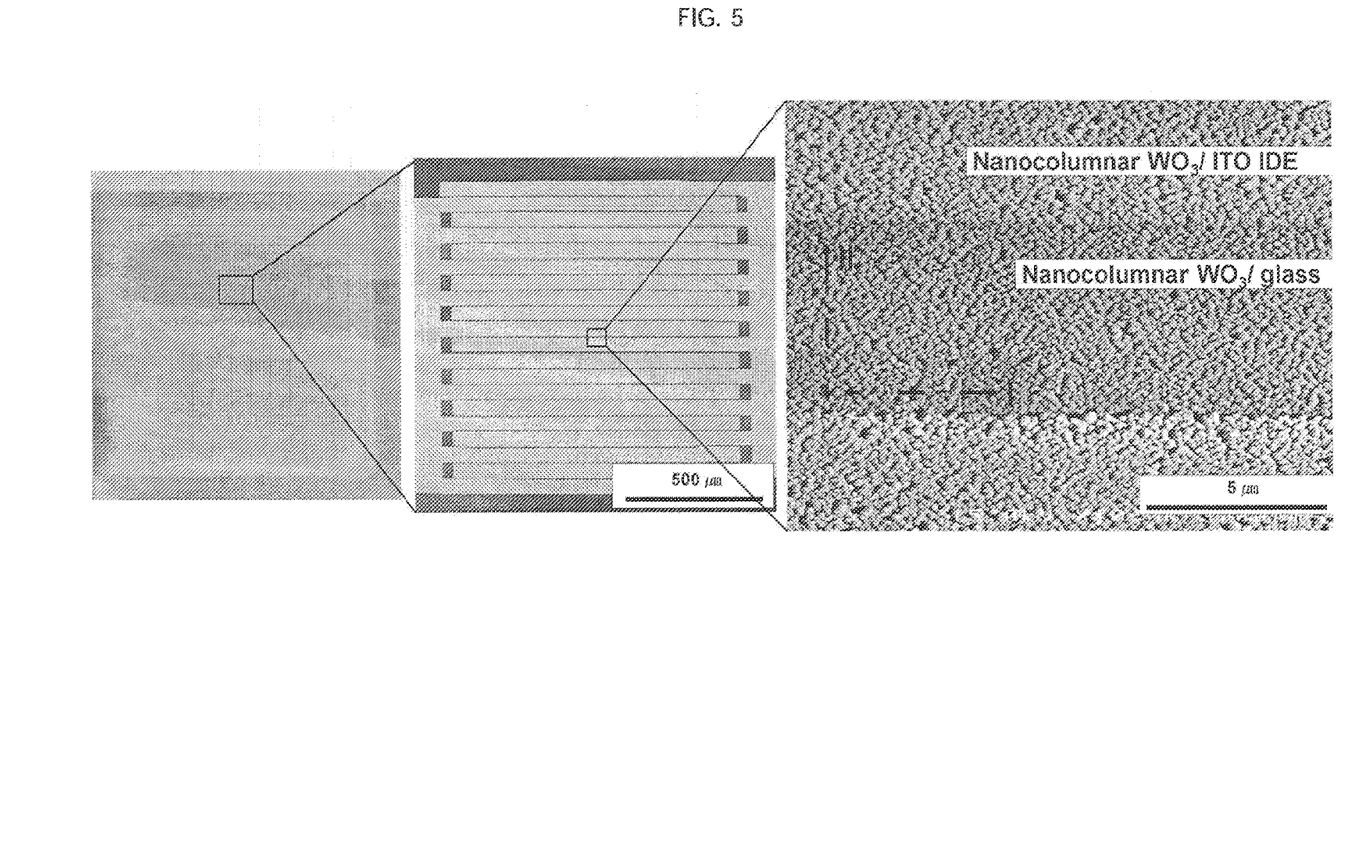
FIG. 5 shows surface images of a transparent gas sensor manufactured according to an exemplary embodiment of the present disclosure.
Figure 6:
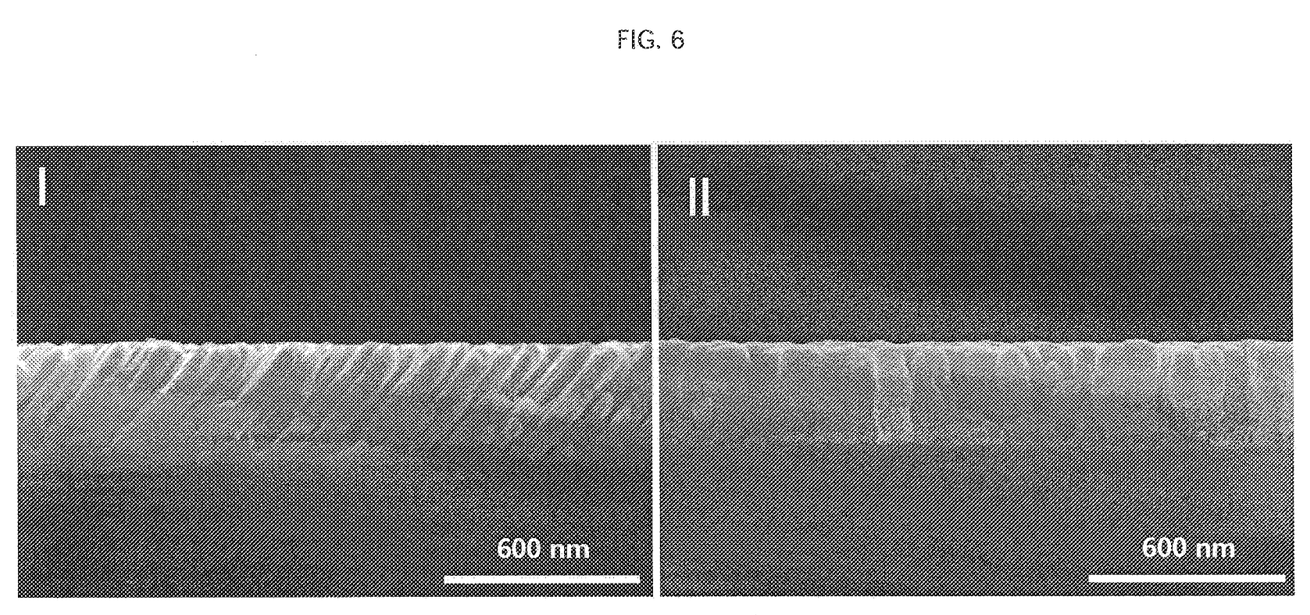
FIG. 6 shows scanning electron microscopic images of a cross-section of a transparent gas sensor manufactured according to an exemplary embodiment of the present disclosure.

FIG. 5 and FIG. 6 show the images of the transparent gas sensor manufactured in Example 1. FIG. 5 shows surface images and FIG. 6 shows cross-sectional scanning electron microscopic images. Although not appreciable from the images of FIG. 5 and FIG. 6, the transparent gas sensor is transparent. The left image of FIG. 6 shows cross-section along the direction I in FIG. 5 (x direction in the x-y plane), and the right image shows cross-section along the direction II in FIG. 5 (y direction in the x-y plane).

As seen from FIG. 5 and FIG. 6, the gas-sensing layer ($WO_3$ layer) has a nanocolumnar structure which is not appreciable with naked eyes. Also, as distinctly seen from FIG. 6, since pores are formed between the nanocolumns arranged in the direction I (x direction), gas can diffuse to the bottom portion of the $WO_3$ layer. And, the nanocolumns arranged in the direction II (y direction) are connected with each other to provide contact between the IDE transparent electrode patterns, allowing easy measurement of electrical resistance between the IDE transparent electrodes.

Figure 7:
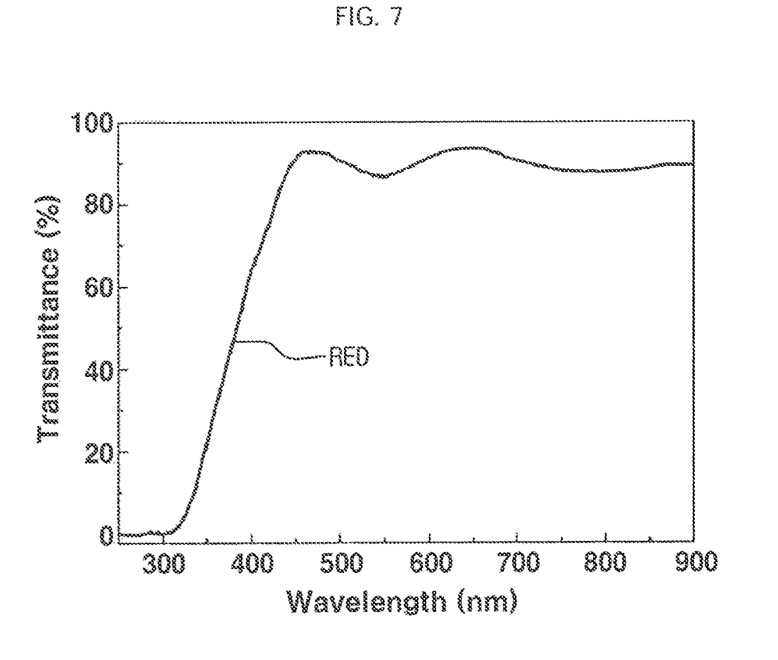
FIG. 7 shows a result of testing light transmittance of a transparent gas sensor manufactured according to an exemplary embodiment of the present disclosure.
Figure 8:
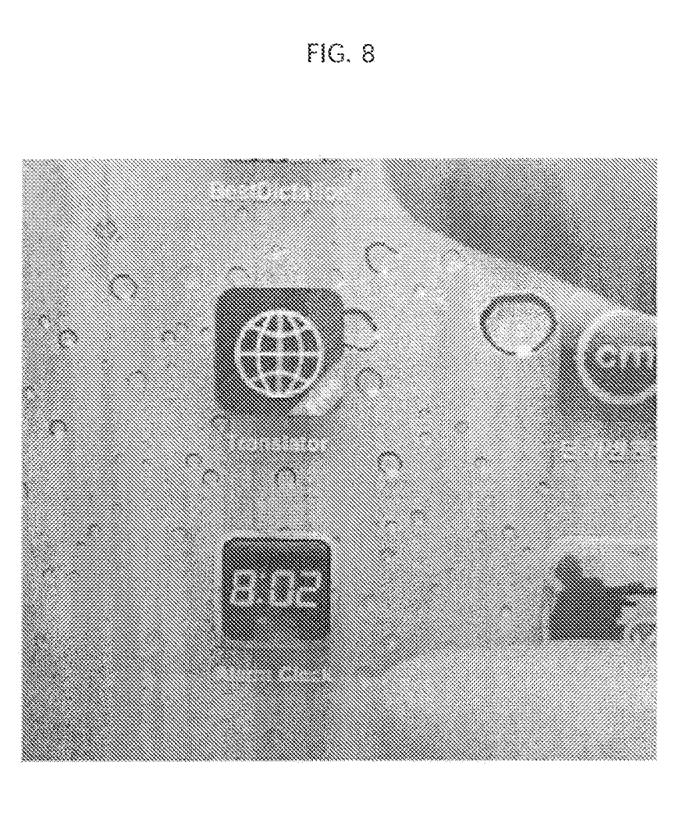
FIG. 8 is an image of a transparent gas sensor manufactured according to an exemplary embodiment of the present disclosure attached on the surface of a mobile terminal.

FIG. 7 shows a result of testing light transmittance of the transparent gas sensor manufactured in Example 1. And, FIG. 8 is an image of the transparent gas sensor manufactured in Example 1 attached on the surface of a mobile terminal.

As seen from FIG. 7, the transparent gas sensor showed high light transmittance close to 90% in the visible region. When the transparent gas sensor was attached on the mobile terminal, the gas sensor was not easily appreciable with naked eyes due to high light transmittance as seen from FIG. 8. Accordingly, the transparent gas sensor can be used for transparent displays or other applications where transparency is required such as windowpanes.

Figure 9:
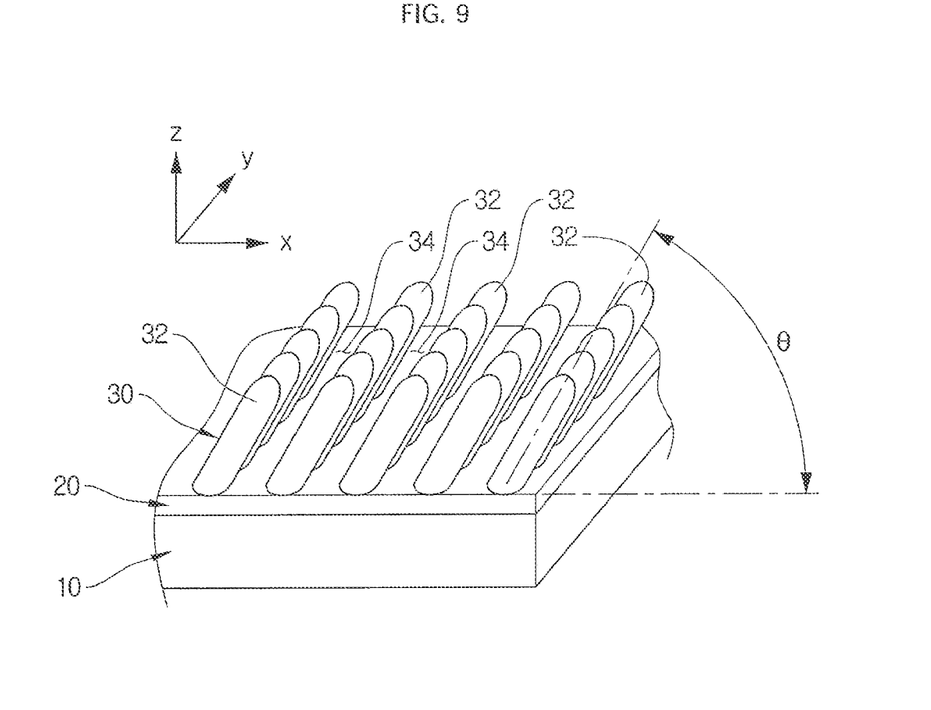
FIG. 9 shows a result of testing response of transparent gas sensors of Example 1 and Comparative Example 1 to CO gas.
Figure 10:
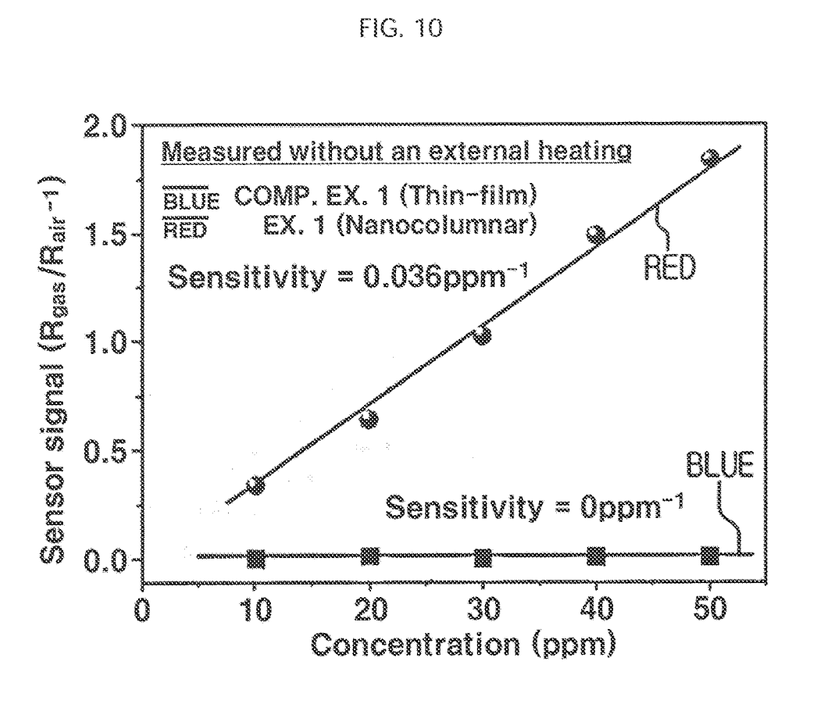
FIG. 10 shows a result of testing sensitivity of transparent gas sensors of Example 1 and Comparative Example 1 to CO gas.

Further, response and sensitivity of the gas sensors manufactured in Example 1 and Comparative Example 1 to CO gas were tested. The result is shown in FIG. 9 and FIG. 10. FIG. 9 shows a result of testing response to CO gas, and FIG. 10 shows a result of testing sensitivity to CO gas.

First, as seen from FIG. 9, Example 1 wherein the $WO_3$ layer has a nanocolumnar structure exhibited distinct response to CO gas even under the low concentration of 10-50 ppm whereas Comparative Example 1 wherein the $WO_3$ layer is formed as a flat thin film showed no response at all.

And, as seen from FIG. 10, the sensitivity of the sensor of Comparative Example 1 wherein the $WO_3$ layer is formed as a flat thin film was 0 $ppm^{-1}$ because there was no response. In contrast, Example 1 wherein the $WO_3$ layer has a nanocolumnar structure exhibited very superior sensitivity of 0.036 $ppm^{-1}$. It is a remarkable result considering that no heat was supplied form outside during the gas detection.

During the test of response of CO gas, power consumption was 0.125 mW, which is remarkably low as compared to that of the existing semiconductor-based thick-film gas sensor (about 1 mW) or MEMS-based thin-film gas sensor (about 10-200 mW). The low power consumption suggests that the transparent gas sensor is easily applicable to mobile devices such as mobile phones.

Figure 11:
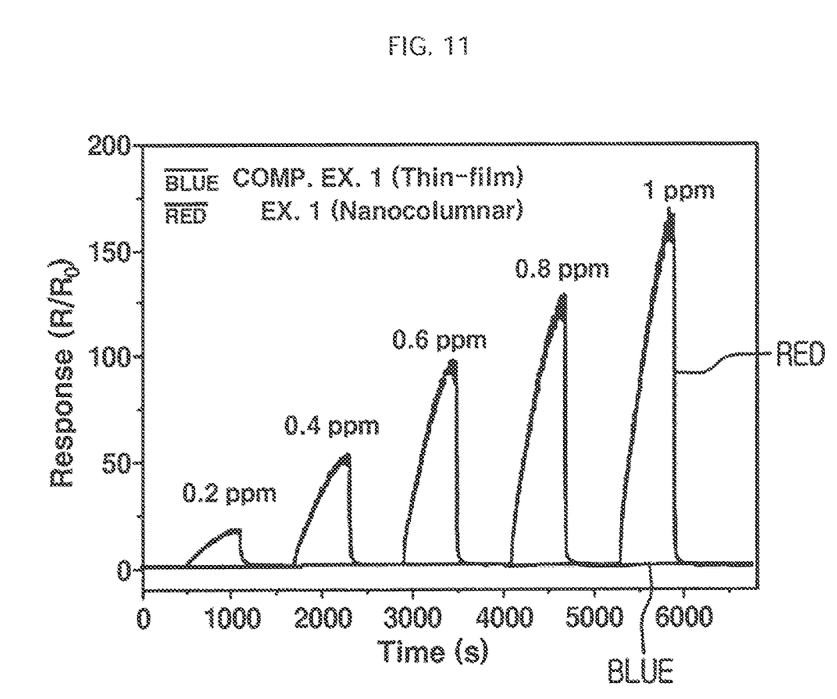
FIG. 11 shows a result of testing response of transparent gas sensors of Example 1 and Comparative Example 1 to $NO_2$ gas.
Figure 12:
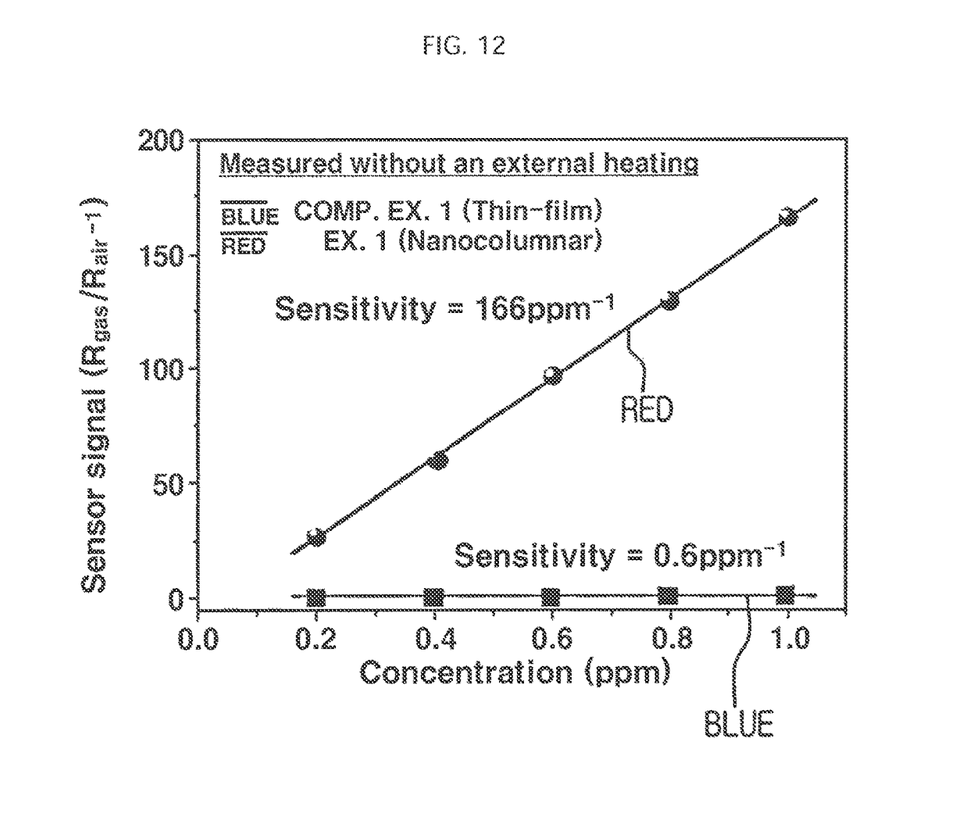
FIG. 12 shows a result of testing sensitivity of transparent gas sensors of Example 1 and Comparative Example 1 to $NO_2$ gas.

Also, response and sensitivity of the gas sensors manufactured in Example 1 and Comparative Example 1 to $NO_2$ gas were tested. The result is shown in FIG. 11 and FIG. 12. FIG. 11 shows a result of testing response to $NO_2$ gas, and FIG. 12 shows a result of testing sensitivity to $NO_2$ gas.

First, as seen from FIG. 11, Example 1 wherein the $WO_3$ layer has a nanocolumnar structure exhibited distinct response to $NO_2$ gas even under the low concentration of 0.1-1 ppm whereas Comparative Example 1 wherein the $WO_3$ layer is formed as a flat thin film showed insignificant response.

And, as seen from FIG. 12, the sensitivity of the sensor of Comparative Example 1 wherein the $WO_3$ layer is formed as a flat thin film was 0.6 $ppm^{-1}$ because the response was insignificant. In contrast, Example 1 wherein the $WO_3$ layer has a nanocolumnar structure exhibited very superior sensitivity of 166 $ppm^{-1}$, as much as 270 times that of Comparative Example 1.

Figure 13:
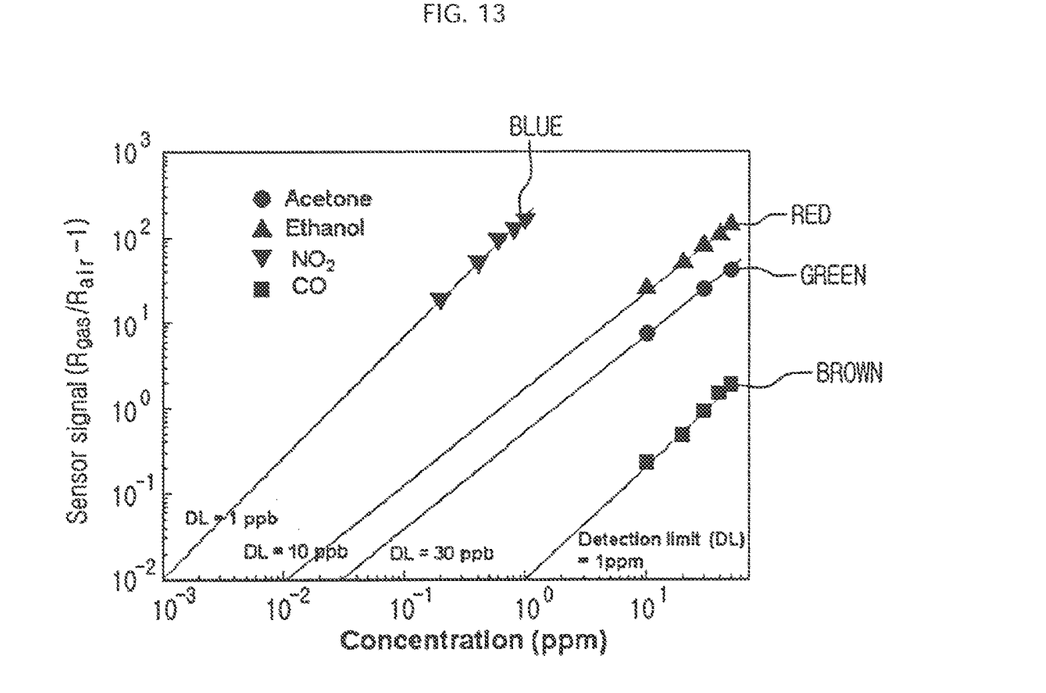
FIG. 13 shows a result of testing detection limit (DL) of a transparent gas sensor according to an exemplary embodiment of the present disclosure for CO, $NO_2$, ethanol and acetone.

FIG. 13 shows a result of testing detection limit (DL) of the transparent gas sensor manufactured in Example 1 for CO, $NO_2$, ethanol and acetone. The detection limit (DL) could be determined since the response to each gas changes linearly with concentration.

As seen from FIG. 13, the detection limit (DL) was very low, with 1 ppm for CO, 1 ppb for $NO_2$, 10 ppb for ethanol, and 30 ppb for acetone. This detection limit (DL) is significantly lower than the air pollution standard of Korea and the WHO [Korean standard: CO (1 hr) 25 ppm, $NO_2$ (1 hr) 100 ppb; WHO standard: CO (1 hr) 25.7 ppm, $NO_2$ (1 hr) 105 ppb].

From the detection limit test result, it can be seen that the transparent gas sensor can be used not only as an air quality sensor for detecting CO, $NO_R$, $H_2$, $H_2O$, $SO_2$, $NH_3$, $O_3$, $H_2S$ and volatile organic compounds (VOCs) but also as a sensor for detecting other harmful gas or toxic gas for counterterrorism.

Examples 2-5

Gas sensors were manufactured as in Example 1 by varying the materials of a gas-sensing layer. Specifically, when forming the gas-sensing layer having a nanocolumnar structure on an IDE transparent electrode by sputtering, different targets were used to form $SnO_2$ layer (Example 2), $Nb_2O_5$ layer (Example 3), ZnO layer (Example 4) and $In_2O_3$ layer (Example 5) as the gas-sensing layer having the nanocolumnar structure on the IDE transparent electrode.

Comparative Examples 2-5

Gas sensors were manufactured as in Comparative Example 1 by varying the materials of a gas-sensing layer. Specifically, different targets were used to form $SnO_2$ layer (Comparative Example 2), $Nb_2O_5$ layer (Comparative Example 3), ZnO layer (Comparative Example 4) and $In_2O_3$ layer (Comparative Example 5) as the gas-sensing layer having the flat thin film on the IDE transparent electrode.

Figure 14:
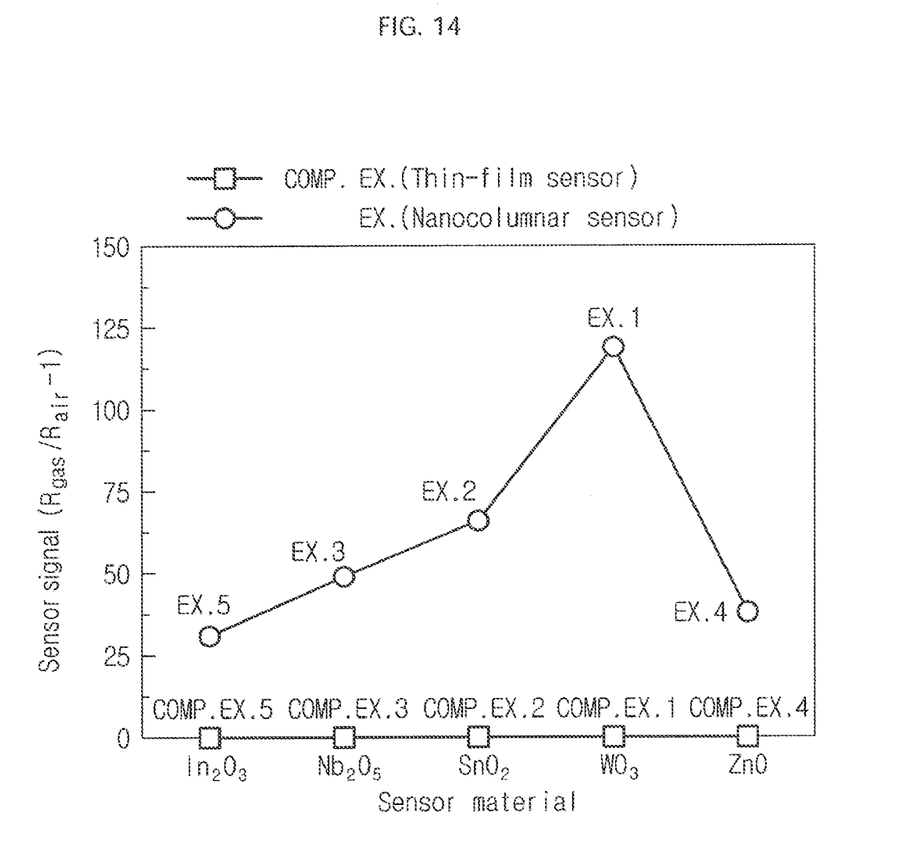
FIG. 14 shows a result of testing response of transparent gas sensors of Examples 1-5 and Comparative Examples 1-5 with different gas-sensing layers to $NO_2$ gas (0.8 ppm).

Response of the gas sensors manufactured in Examples 2-5 and Comparative Examples 2-5 to $NO_2$ gas (0.8 ppm) was tested. The result is shown in FIG. 14. The test result for Example 1 ($WO_3$) and Comparative Example 1 ($WO_3$) is also given in FIG. 14.

As seen from FIG. 14, Examples 1-5 wherein the gas-sensing layer has a nanocolumnar structure exhibited distinct response to $NO_2$ gas (0.8 ppm) whereas Comparative Examples 1-5 wherein the gas-sensing layer is formed as a flat thin film showed insignificant response to $NO_2$ gas (0.8 ppm).

As demonstrated through the above examples, the transparent gas sensor wherein the gas-sensing layer has a nanocolumnar structure exhibits excellent response as well as very superior gas sensitivity. By forming the gas-sensing layer to have the nanocolumnar structure via a simple process, very superior gas sensitivity can be achieved even when no heat is supplied from outside.

Also, since the transparent gas sensor is highly transparent with light transmittance of at least 90% in the visible region, it is applicable to transparent displays or other applications where transparency is required such as windowpanes. In addition, since it consumes less power, it can be used for mobile devices such as mobile phones.

In addition, the transparent gas sensor can be produced in large scale since both the transparent electrode and the gas-sensing layer comprise metal oxide and can be formed by the same deposition process. Besides, since the transparent gas sensor does not require the expensive noble metal electrode and the production process is compatible, it can be produced at low cost.

While the present disclosure has been described with respect to the specific embodiments, it will be apparent to those skilled in the art that various changes and modifications may be made without departing from the spirit and scope of the disclosure as defined in the following claims.

What is claimed is:

1. A transparent gas sensor comprising:
a transparent substrate;
a transparent electrode formed on the transparent substrate; and
a transparent gas-sensing layer formed on the transparent electrode, wherein the transparent gas-sensing layer has a nanocolumnar structure comprising nanocolumns formed on the transparent electrode and gas diffusion pores formed between the nanocolumns,
wherein the nanocolumns are formed to be inclined with an angle of 60-89° by glancing angle deposition, and the gas diffusion pores are formed in a self-shadowed region where the deposition does not occur.

2. The transparent gas sensor according to claim 1, wherein the nanocolumns are arranged on an x-y plane on the transparent electrode such that the gas diffusion pores are formed between the nanocolumns arranged in one of the x and y directions and the nanocolumns arranged in the other direction are connected with each other.

3. The transparent gas sensor according to claim 1, wherein the transparent gas-sensing layer comprises a metal oxide having a band gap of at least 2.7 eV.

4. The transparent gas sensor according to claim 1, wherein the transparent gas-sensing layer comprises at least one metal oxide selected from tungsten oxide ($WO_3$), tin oxide ($SnO_2$), niobium oxide ($Nb_2O_5$), zinc oxide (ZnO), indium oxide ($In_2O_3$), iron oxide ($Fe_2O_3$), titanium oxide ($TiO_2$), cobalt oxide ($Co_2O_3$) and gallium oxide ($Ga_2O_3$).

5. The transparent gas sensor according to claim 1, wherein the transparent substrate is a glass, sapphire, quartz or MgO substrate.

6. The transparent gas sensor according to claim 1, wherein the transparent electrode is metal oxide film or carbon film.

7. The transparent gas sensor according to claim 6, wherein the transparent electrode is a metal oxide film, wherein the metal oxide film is an oxide film comprising at least one metal selected from indium (In), tin (Sn), zinc (Zn), aluminum (Al), niobium (Nb), titanium (Ti) and gallium (Ga).

8. The transparent gas sensor according to claim 6, wherein the transparent electrode is a metal oxide film, wherein the metal oxide film is an oxide film selected from indium tin oxide (ITO), fluorine tin oxide (FTO), aluminum zinc oxide (AZO), gallium zinc oxide (GZO), indium zinc oxide (IZO) and niobium titanium oxide (NTO).

9. The transparent gas sensor according to claim 6, wherein the transparent electrode is a carbon film, wherein the carbon film comprises graphene.

* * * * *